United States Patent [19]

Subluskey

[11] 3,980,717

[45] Sept. 14, 1976

[54] MANUFACTURE OF PARA-NITRO-META-CRESOL FROM META/PARA-CRESOL MIXTURES

[75] Inventor: Lee A. Subluskey, Hockessin, Del.

[73] Assignee: Hercules Incorporated, Wilmington, Del.

[22] Filed: June 30, 1971

[21] Appl. No.: 158,594

[52] U.S. Cl............................................. 260/622 R
[51] Int. Cl.² ........................................ C07C 79/26
[58] Field of Search...................... 260/622 R, 622 P

[56] References Cited
UNITED STATES PATENTS 3,510,527  5/1970  Prosser .............................. 260/622

FOREIGN PATENTS OR APPLICATIONS 1,165,637  10/1969  United Kingdom................. 260/622
872,184    7/1961   United Kingdom................. 260/622
1,142,300  5/1969   United Kingdom................. 260/622

Primary Examiner—James O. Thomas, Jr.
Assistant Examiner—W. B. Lone
Attorney, Agent, or Firm—George H. Hopkins

[57] ABSTRACT

Process for the manufacture of para-nitro-meta-cresol in high yield from directly available and inexpensive meta/para-cresol mixtures, without need heretofore for first resolving the cresol mixture to provide a separate meta-cresol reactant.

The process comprises subjecting the cresol mixture to nitration, whereby para-nitro-meta-cresol is formed, and then separating the para-nitro-meta-cresol from the resulting nitration reaction mixture.

In one embodiment, the cresol mixture is introduced into reaction with an aqueous acid mixture containing $HNO_3$ and $HNO_2$ as the only acid ingredients, under defined critical conditions of feed flow rate, temperature, acid concentrations, and reactant proportions to provide the cresol nitration reaction product mixture.

11 Claims, No Drawings

MANUFACTURE OF PARA-NITRO-META-CRESOL FROM META/PARA-CRESOL MIXTURES

This invention relates to the manufacture of para-nitro-meta-cresol. In one aspect this invention relates to the nitration of meta/para-cresol mixtures (m/p-cresols) to form para-nitro-meta-cresol for separation and recovery as chief nitration product. In still another aspect this invention relates to a method for separation of components of meta/para-cresol mixtures as nitro-isomers, including para-nitro-meta-cresol as principal nitro-isomer product. Other aspects will be apparent in light of the accompanying disclosure and the appended claims.

Cresols are obtained from coal tar and petroleum as various grades of mixed meta-, para-, and ortho-, cresols. Although o-cresol is readily separated from the cresol mixture by ordinary fractional distillation, the separation of residual meta-, and para-, cresols has not been commercially feasible, due to the close similarity of their physical properties. Accordingly, the meta- and para-isomers are generally utilized as m/p-cresols rather than to employ costly and unsatisfactory separation procedures that have been proposed; and hence the ultimate use of those cresols has been a function of the mixture in lieu of the cresols separately.

Para-nitro-meta-cresol has utility in numerous applications, particularly as an intermediate in the manufacture of agricultural chemicals; and heretofore it has been manufactured directly from meta-cresol as an isolated meta-cresol reactant.

This invention is concerned with the manufacture of para-nitro-meta-cresol in high yield from directly available and inexpensive m/p-cresol mixtures, without the need heretofore for first resolving the cresol mixture to provide the separate meta-cresol reactant.

In accordance with the invention, a mixture of meta-, and para-, cresols is subjected to nitration, whereby para-nitro-meta-cresol is formed, and said para-nitro-meta-cresol is separated from the resulting nitration reaction mixture as product.

Any suitable nitration procedure known in the art can be utilized in practice of the invention, as for example reaction of the creasol mixture with nitric acid in glacial acetic acid, nitration in accordance with the multistage process disclosed in U.S. Pat. No. 3,510,527 involving reaction of the phenolic in an aqueous nitric acid/nitrous acid system, and nitration in accordance with the single stage process disclosed in U.S. Pat. No. 3,519,693 involving reaction of the phenolic in an aqueous nitric acid/nitrous acid/sulfuric acid system.

In accordance with one embodiment of the invention the m/p-cresol mixture is introduced into reaction with an aqueous acid mixture containing $HNO_2$ and $HNO_3$ as the only acid ingredients, while maintaining the resulting reaction temperature within the range of from $-15°$ to $+15°C$., and at a rate permitting substantially immediate conversion of intermediately formed nitrosocresol to nitrocresol; said aqueous acid mixture, prior to introducing said cresol mixture into said reaction, containing about $0.2 - 3$ moles per liter of said $HNO_2$ and about $2.3 - 10$ moles per liter of said $HNO_3$, and containing each said acid in a mole ratio of total cresols introduced into said reaction within the respective ranges of about $0.4:1 - 1:1$ ($HNO_2$/cresols) and about $4:1 - 5:1$ ($HNO_3$/cresols); and recovering para-nitro-meta-cresol as product.

The above described mole ratios of $HNO_2$ and $HNO_3$ to total cresols introduced into the reaction are often within the respective ranges of about $0.5:1 - 0.95:1$ ($HNO_2$/cresols) and about $4.2:1 - 4.8:1$ ($HNO_3$/cresols) but are generally within the respective ranges of about $0.7:1 - 0.9:1$ and about $4.3:1 - 4.6:1$. The reaction temperature is generally at least $0°C$., and often within the range of from 5 to $15°C$. The above described $HNO_2$ and $HNO_3$ concentrations (moles per liter) are often within the respective ranges of about $0.5 - 1$ ($HNO_2$) and about $3 - 6$ ($HNO_3$), but are generally within the respective ranges of about $0.8 - 1$ and about $4 - 5$.

In preferred practice the aqueous acid mixture is formed by addition of one or more oxides of nitrogen to an aqueous $HNO_3$ solution for reaction therein to form the $HNO_2$ acid component, the aqueous $HNO_3$ solution initially containing $HNO_3$ and water in sufficient proportions for both the $HNO_2$-forming and the nitration, reactions. The nitrogen oxide(s) can be added to the aqueous nitric acid mixture, as a gas stream, although nitrogen trioxide and nitrogen tetroxide are often advantageously added as liquids. Reaction of nitrogen oxide(s) in the aqueous nitric acid solution are illustrated with reference to the equations:

$$2NO + HNO_3 + H_2O \rightarrow 3HNO_2 \qquad (1)$$

$$N_2O_4 + H_2O \rightarrow HNO_2 + HNO_3 \qquad (2)$$

$$N_2O_3 + H_2O \rightarrow 2HNO_2 \qquad (3)$$

Although the cresol-aqueous acid reaction can be carried out in any suitable manner, it is preferred to first form the acid mixture by admixing the water and nitric acid ingredients followed by the addition of the nitrogen oxide for the $HNO_2$ formations, and then introducing an aqueous strem of the cresol mixture directly into a body of the acid mixture for the requisite time period, often in the order of from 2 to 4 hours.

During introduction of the mixed cresols into the body of aqueous acid, the resulting reaction mixture is maintained under suitable agitation conditions within the requisite temperature range, vigorous stirring of the reaction mixture generally being sufficient for the degree of agitation required. Nitrosocresol intermediate is formed during the reaction and it is essential that the rate of introduction of the mixed cresols into the aqueous acid mixture be limited in order that all nitrosocresol intermediate product be permitted to react substantially immediately in order to prevent accumulation of the nitrosocresol intermediate with accompanying undue thickening and concomitant processing difficulties, particularly those involving loss of control in agitation and cooling, and hence accompanying decrease in efficiency of the reaction and loss in nitroisomer product yields. Under these conditions, all nitrosocresol intermediate is promptly converted to nitrocresol product. Total nitrocresol product is substantially insoluble in the reaction mixture under the reaction conditions and hence is suspended therein as a slurry.

The nitration reaction mixture, at the end of the cresol addition period is advantageously maintained at, or near, its reaction temperature level for an extended period, say from 5 to 40 minutes, in order to assure substantially complete reaction. Subsequent to that extended period, it is often further advantageous to permit the reaction temperature to rise to about 15° – 25°C. to further assure substantially complete reaction. The resulting reaction mixture is filtered at a temperature within the reaction temperature range, generally at about +5°C., or somewhat lower, for recovery of total solid reaction product.

Dependent upon the particular source of the m/p-cresol mixture, the relative proportions of the two nitroisomers are variable over an appreciable range. However, the mole ratio of m-cresol to p-cresol in the m/p-cresol reactant mixture is often within the range of about 0.6:1 – 4:1.

The following illustrates total nitrocresol product, including para-nitro-meta-cresol as chief product formed in accordance with process of the invention.

| Moles Per Mole of m/p-Cresols[1] | |
|---|---|
| Nitroisomer Product | |
| p-nitro-m-cresol | 0.3 – 0.6 |
| 2-nitro-m-cresol | |
| 6-nitro-m-cresol | 0.16 – 0.27 |
| 2-nitro-p-cresol | |
| 2,6-dinitro-m-cresol | |
| 4,6-dinitro-m-cresol | 0 – 0.10 |
| 2,4-dinitro-m-cresol | |
| 2,6-dinitro-p-cresol | |

[1] m-cresol:p-cresol mole ratio within the range of from 1:1 – 4:1

EXAMPLE 1

A mixture of 0.75 moles of m/p-cresols having a meta- to para- mole ratio of 60/40, is reacted in an aqueous nitrous acid/nitric acid system with stirring, in a jacketed glass reactor. The reactor is equipped with a bottom stopcock, and with condenser, stirrer, and thermometer, each extending into a reactor interior through suitable joints in the top reactor wall. Also included in the reactor system is a tube extending from direct communication with the reactor interior, through the top to a Fractol bubbler, and two reagent addition funnels extending into the reactor interior through the top reactor wall, of which one is a standard dropping funnel and the other a dropping funnel jacketed for circulation of cooling fluid.

The reactor is charged with 500 ml of water and 170 ml (2.70 moles) of 70 percent nitric acid. Nitrogen is then flushed through the entire reactor system. 1.28 moles of nitrogen dioxide is condensed, and, as liquid $N_2O_4$ (39 ml, 0.64 moles) collected directly in the jacketed additional funnel, the latter having been cooled by circulation of cooling fluid through the funnel jacket. Pressure in the reactor is regulated by nitrogen flow through the reactor, set to cause a continuous flow of bubbles in the Fractol regulator, the internal reactor pressure being about 60 mm Hg. The resulting aqueous acid admixture ($HNO_3$ - $HNO_2$) is then cooled to +5°C. by circulation of a chilled cooling liquid through the reactor jacket.

Under nitrogen pressure, the liquid $N_2O_4$ (39 ml) is added dropwise, from the dropping funnel, into the aqueous nitric acid mixture. Thereafter, 81 grams of the m/p-cresol charge (60 percent m-cresol, 40 percent p-cresol) is added dropwise, under nitrogen pressure, to the aqueous acid mixture, substantially continuously over a 3 hour period. At the end of the cresol addition period, the resulting slurry reaction mixture is stirred for an additional ½ hour at +5°C. to assure completion of the cresol-acid mixture reaction. The reaction mixture is then drained from the bottom of the reactor onto a Buchner funnel with collection of total crude solid nitration product by suction filtration. The crude solid product cake is then dried in a vacuum desiccator. Typical analysis of the dried crude product, by gas chromatography, shows 4-nitro-m-cresol 52.5 percent; 4-nitroso-m-cresol about 1 percent or less; 2-nitro-p-cresol and 6-nitro-m-cresol, combined, 32.4 percent. The yield of 4-nitro-m-cresol, based on the amount of m-cresol in the m/p-cresol introduced into the aqueous acid mixture, is 68 percent.

As is well known, various nitrophenolic compounds present thermal explosive hazards, and it is important that such compounds be handled with full awareness of the degree of potential explosive hazard involved. p-nitro-m-cresol potentially presents such thermal explosive hazards under temperature conditions that would be required for its recovery by distillation, and it is accordingly advisable that it be recovered from the nitration reaction mixture by non-distillation means. Thus, recovery of p-nitro-m-cresol by solvent extraction from the total solids product is advantageously utilized with separation of the p-nitro-m-cresol product from the extract phase by crystallization and evaporation of the sovlent. One now preferred procedure is that utilizing a benzene-aqueous sodium sulfite extraction solvent, followed by separation of, and then cooling, the benzene phase to precipitate crystalline p-nitro-m-cresol product therefrom, as illustrated with reference to Example 2.

EXAMPLE 2

Crude dried solid product cake formed, and recovered from a Buchner funnel system, as described with reference to Example 1, is processed for recovery of pure 4-nitro-m-cresol in accordance with the following procedure:

Fifty grams of the crude frozen solid cake product is mixed with 500 ml of benzene to which is then added 5 grams of sodium sulfite in 10 ml of water. The resulting benzene-sulfite admixture is stirred rapidly and heated slowly to 60°C. and then allowed to settle at ambient temperature to form separate aqueous and hydrocarbon liquid phases. The aqueous phase layer is removed, and the benzene layer is cooled so as to precipitate crystalline solids therefrom, followed by filtration to yield 19.15 grams of benzene-damp light crystals. The crystal product material, by gas chromatography analysis, contains 79.9 percent 4-nitro-m-cresol with less than 0.5 percent o-nitro-cresol. Evaporation of the benzene mother liquor affords an additional 6.3 grams of crystalline solid. The yield of pure 4-nitro-m-cresol, based on the amount of m-cresol in the m/p-cresols introduced into the aqueous acid mixture, is 65 percent.

Alternatively, in carrying out procedure illustrated with reference to Example 2, the p-nitro-m-cresol can be recovered by distillation of the benzene from the separated benzene phase to provide residual p-nitro-m-cresol product.

As will be evident to those skilled in the art, various modifications can be made or followed, in light of the foregoing disclosure and discussion, without departing from the spirit or scope of the disclosure or from the scope of the claims.

What I claim and desire to protect by Letters Patent is:

1. A process for separating m-cresol moiety and p-cresol moiety in a mixture of m- and p-cresols, which comprises subjecting said mixture to nitration whereby a reaction mixture comprising at least p-nitro-m-cresol is formed, and separating from said reaction mixture a product consisting essentially of p-nitro-m-cresol.

2. In a process of claim 1, introducing said mixture of cresols into an aqueous acid mixture containing $HNO_2$ and $HNO_3$ as the only acid ingredients, while maintaining the resulting reaction temperature within the range from −15° to +15°C., and at a rate at which no substantial accumulation of nitrosocresol occurs, said aqueous mixture, prior to introduction of said mixture of cresols into it, containing $HNO_2$ at about 0.2 – 3 moles per liter and $HNO_3$ at about 2.3 – 10 moles per liter with the mole ratio of $HNO_2$ to total cresols introduced into said aqueous acid mixture being about 0.4:1 – 1:1 and with the mole ratio of $HNO_3$ to total cresols introduced into said aqueous acid mixture being about 4:1 – 5:1.

3. A process of claim 2 wherein said temperature is at least as high as 0°C., the mole ratio of $HNO_2$ to total cresols introduced into said aqueous acid mixture is about 0.5:1 – 0.95:1, the mole ratio of $HNO_3$ to total cresols introduced into said acid mixture is about 4.2:1 – 4.8:1, the concentration of $HNO_2$ in said acid mixture is about 0.5 – 1 mole per liter, the concentration of $HNO_3$ in said acid mixture is about 3 – 6 moles per liter and said mixture of cresols is introduced into said aqueous acid mixture over a period of 2 – 4 hours.

4. A process of claim 3 wherein said temperature is within the range from 5° to 15°C., the mole ratio of $HNO_2$ to total cresols introduced into said acid mixture is about 0.7:1 – 0.9:1, the mole ratio of $HNO_3$ to total cresols introduced into said acid mixture is about 4.3:1 – 4.6:1, the concentraton of $HNO_2$ in said acid mixture is about 0.8 – 1 mole per liter, and the concentration of $HNO_3$ in said acid mixture is about 4 – 5 moles per liter.

5. A process of claim 4 wherein the mole ratio of m-cresol to p-cresol in said mixture of cresols is about 0.6:1 – 4:1.

6. In a process of claim 2, separating p-nitro-m-cresol from said product by solvent extraction.

7. In a process of claim 2, after introducing said mixture of cresols into said aqueous acid mixture, maintaining the resulting reaction mixture in said temperature range for an additional time period of from 5 to 40 minutes.

8. In a process of claim 7, after said additional time period, increasing the temperature of said reaction mixture to the range of 15° to 25°C., cooling said reaction mixture to −15° to 15°C. and separating solid p-nitro-m-cresol.

9. In a process of claim 2, admixing said product with benzene and water containing in solution sodium sulfite, allowing phase separation to take place in the resulting mixture, separating benzene phase, and recovering p-nitro-m-cresol from separated benzene phase.

10. In a process of claim 9, recovering p-nitro-m-cresol from separated benzene phase by cooling said separated benzene phase until p-nitro-m-cresol has precipitated, and separating precipitated p-nitro-m-cresol from said benzene phase.

11. In a process of claim 9, recovering p-nitro-m-cresol from said benzene phase by distilling substantially all of the benzene from said benzene phase.

* * * * *